United States Patent
Woo et al.

(10) Patent No.: US 11,857,586 B2
(45) Date of Patent: Jan. 2, 2024

(54) **PHARMACEUTICAL COMPOSITION FOR PREVENTING OR TREATING GYNECOLOGICAL DISEASES CONTAINING *SARCODON ASPRATUS* EXTRACTS AS ACTIVE INGREDIENT**

(71) Applicant: Hye Jin Woo, Yangsan-si (KR)

(72) Inventors: Hye Jin Woo, Yangsan-si (KR); Dae Ha Woo, Yangsan-si (KR)

(73) Assignee: Hye Jin Woo, Yangsan-si (KR)

(*) Notice: Subject to any disclaimer, the term of this patent is extended or adjusted under 35 U.S.C. 154(b) by 0 days.

(21) Appl. No.: 17/963,888

(22) Filed: Oct. 11, 2022

(65) Prior Publication Data
US 2023/0050522 A1    Feb. 16, 2023

Related U.S. Application Data

(62) Division of application No. 16/496,159, filed as application No. PCT/KR2018/002529 on Mar. 2, 2018, now abandoned.

(30) Foreign Application Priority Data

Mar. 23, 2017    (KR) ........................ 10-2017-0037168

(51) Int. Cl.
*A61K 36/07*    (2006.01)
*A61P 15/08*    (2006.01)
*A61K 9/00*    (2006.01)

(52) U.S. Cl.
CPC ............ *A61K 36/07* (2013.01); *A61K 9/0056* (2013.01); *A61P 15/08* (2018.01); *A61K 2236/333* (2013.01)

(58) Field of Classification Search
None
See application file for complete search history.

(56) References Cited

U.S. PATENT DOCUMENTS

2016/0367614 A1    12/2016    Kim

FOREIGN PATENT DOCUMENTS

| CN | 106333159 A | | 1/2017 |
|---|---|---|---|
| CN | 106333163 A | * | 1/2017 |
| KR | 10-2015-0089188 A | | 8/2015 |
| KR | 10-1598283 B1 | | 2/2016 |
| KR | 10-2016-0058270 A | | 5/2016 |
| KR | 20160108771 A | * | 9/2016 |
| KR | 20160108771 A | | 9/2016 |
| KR | 10-2017-0028486 A | | 3/2017 |

OTHER PUBLICATIONS

Lee, H.J. et al., "Physiological Properties of Sarcodon aspratus Extracts by Ethanol Concentration," Journal of the Korean Society of Food Science and Nutrition, vol. 43, Issue 5, pp. 656-660 (May 2014) (English Abstract).
Kang, H.C. et al., "Chemical structures of the compounds isolated from edible mushroom sarcodon aspratus," Journal of Korean Agricultural Chemical Society, vol. 43, No. 4, pp. 298-302 (2000) (English Abstract).
Nootropics (https://nootropicsdepot.com/articles/mushroom-extracts-whole-fruiting-bodies-vs-mycellium-on-graiin/#:~:text=Fruiting%20bodies%20offer%20a%20mcuh,of%20the%20mushroom's%20nutritional%20components.) Mar. 28, 2016.

* cited by examiner

*Primary Examiner* — Terry A McKelvey
*Assistant Examiner* — Jacob A Boeckelman
(74) *Attorney, Agent, or Firm* — Maschoff Brennan

(57) ABSTRACT

The present invention relates to a composition for prevention or treatment of gynecological diseases containing an extract of *Sarcodon imbricatus* as an active ingredient. Specifically, the extract of *Sarcodon imbricatus* of the present invention can be effectively used, with only one dose, for prevention or treatment of gynecological diseases by treating dysmenorrhea, reducing a menstrual period, an amount of menstruation, menstrual irregularity, and extravasated blood, and clearing the color of menstruation.

2 Claims, No Drawings

PHARMACEUTICAL COMPOSITION FOR PREVENTING OR TREATING GYNECOLOGICAL DISEASES CONTAINING *SARCODON ASPRATUS* EXTRACTS AS ACTIVE INGREDIENT

TECHNICAL FIELD

The present invention relates to a pharmaceutical composition for preventing or treating gynecological diseases, the pharmaceutical composition containing *Sarcodon aspratus* extracts as active ingredients.

BACKGROUND ART

In recent years, as women's entry into society is prominent, the number of professional women is increasing. Along with these social phenomena, it is easy to lose nutritional and hormonal balance in the body due to increased intake of Western-style food and fast food, stress at work and home, and excessive dieting. As a result, many women suffer from various diseases such as menstrual irregularity, dysmenorrhea, skin trouble, insomnia, alopecia, depression, and poor growth of the kidneys and breasts.

For treatment or these diseases, hormone replacement therapy, in which artificially synthesized estrogen is administered to the body, is most commonly used. However, it has been reported that long-term treatment with the above therapy may cause uterine cancer, breast cancer, venous thrombosis, gallbladder diseases, and the like. Accordingly, use of hormone replacement therapy is limited.

Dysmenorrhea is one of the most common gynecological diseases, and about 50% of women of childbearing age suffer from dysmenorrhea. Dysmenorrhea occurs first within 1 to 2 years after menarche, and is common among women in their teens or twenties. In some cases, dysmenorrhea may persist after age 40. About 10% of women with dysmenorrhea suffer from severe pain, which prevents them from performing their usual work for one to three days each month.

Dysmenorrhea begins at an upper region of the pubic region several hours before or just before menstruation, and persists for two to three days. Primary dysmenorrhea is caused by excessive contraction of the uterus muscles. In this regard, dysmenorrhea is similar to birth pain. Pain may occur in the coccyx area (lumbar and sacrum) or in front of the thighs during dysmenorrhea. At the same time, symptoms such as vomiting, nausea, and diarrhea may occur, and in rare cases, dysmenorrhea may lead to fainting. In addition, dysmenorrhea, unlike pain caused by intraperitoneal inflammation, is similar to squeezing pain. Dysmenorrhea may be alleviated by massaging a pelvic area or by physical activity, but medication is required when symptoms are severe.

According to the findings from the Oriental Hospital of Kyung Hee Medical Center, at menstruation, 47% of subjects complained of pain such as abdominal pain, backache, and headache, 13% suffered from gastrointestinal disorders such as anorexia and dyspepsia, and 8% felt uncomfortable. In particular, according to a survey of 632 girls in middle and high schools, 70% complained of dysmenorrhea, and 50% complained of severe pain. However, 66% of the girls who participated in the survey were found to simply tolerate pain, and 28% were found to take painkillers. That is, more than 90% of the girls in the survey did not receive fundamental treatment.

Although the mechanism of dysmenorrhea is not yet fully understood, primary dysmenorrhea is known to be caused mostly by increased production of prostaglandin in endometrial cells. In the luteal phase, cyclooxygenase (COX) activity is increased in endometrial cells that are eliminated due to decreased in progesterone levels, and as a result, prostaglandins (PGs), in particularly PGF2-α and PGE2, are secreted. The action of these prostaglandins increases tension in the uterus, and the uterus exhibits high amplitude contraction. At this time, ischemic pain is generated by the contraction.

There is no method for fundamentally treating dysmenorrhea. However, currently, aspirin, ibuprofen, acetaminophen, and the like are commonly used to alleviate pain by inhibiting the production of prostaglandins. However, these drugs may cause side effects such as drug resistance, dyspepsia, nausea, vomiting, constipation, diarrhea, headache, dizziness, visual disturbance, hearing defect, drowsiness, fatigue, and gastrointestinal bleeding.

Therefore, research is being actively conducted to develop a substance that can alleviate dysmenorrhea without side effects. In this regard, "COMPOSITION FOR TREATING PREMENSTRUAL SYNDROME AND ALLEVIATING DYSMENORRHEA CONTAINING GINSENG FRUIT EXTRACTS" was disclosed in Korean Patent Application Publication No. 10-2015-005430, and "USE OF ACECLOFENAC AND SCOPOLAMINE FOR ALLEVIATING OR TREATING DYSMENORRHEA" was disclosed in Korean Patent No. 10-1598283.

Meanwhile, mushrooms are a biological resource that humans have used as food and medicine for thousands of years. Since mushrooms contain polysaccharides, which are metabolites, polysaccharide-peptide complexes, triterpenoids, and proteins, mushrooms have the ability to regulate various physiological responses, and thus mushrooms have important pharmacological value.

Among these mushrooms, *Sarcodon aspratus* is a basidiomycete mushroom belonging to the family Thelephoraceae of the order Aphyllophorales. The height of the fruit bodies of *Sarcodon aspratus* is 10 to 20 cm, the fruit bodies have a funnel shape that spreads like a morning glory, and many trichomes are formed on the fruit bodies. In addition, the diameter of the cap of *Sarcodon aspratus* is 7 to 25 cm, the height of *Sarcodon aspratus* is 7 is to 25 cm, the surface of *Sarcodon aspratus* is rough, and large scales are formed on the surface of *Sarcodon aspratus*. When *Sarcodon aspratus* is dried, strong aroma emitted. Thus, *Sarcodon aspratus* is also referred to as a fragrant mushroom.

*Sarcodon aspratus* is known to be effective in preventing or treating adult diseases such as cancer, stroke, and heart disease by regulating biological functions. *Sarcodon aspratus* forms ectotrophic mycorrhiza with oak roots, and is a mushroom that lives in clusters or alone on the ground of deciduous forests. So far, artificial cultivation of *Sarcodon aspratus* is impossible, and *Sarcodon aspratus* is harvested from nature.

Therefore, the present inventors have tried to develop a therapeutic agent for alleviating and treating dysmenorrhea without side effects. Through the study, the present inventors confirmed that *Sarcodon aspratus* extracts alleviated dysmenorrhea, decreased a menstruation period, the amount of menstrual blood, menstrual irregularity, and the amount of extravasated blood, and cleared the color of menstrual blood. Based on these findings, the prevent inventors completed the present invention.

DISCLOSURE

Technical Problem

Therefore, the present invention has been made in view of the above problems, and it is one object of the present invention to provide *Sarcodon aspratus* extracts for the purpose of preventing or treating gynecological diseases.

Technical Solution

In accordance with one aspect of the present invention, provided is a pharmaceutical composition for preventing or treating gynecological diseases including *Sarcodon aspratus* extracts as active ingredients.

In accordance with another aspect of the present invention, provided is a functional health food for preventing or treating gynecological diseases including *Sarcodon aspratus* extracts as active ingredients.

In accordance with still another aspect of the present invention, provided is a method of preventing or treating gynecological diseases including a step of administering *Sarcodon aspratus* extracts to a subject.

In accordance with yet another aspect of the present invention, provided is a use of *Sarcodon aspratus* extracts for preparation of a pharmaceutical composition for preventing or treating gynecological diseases.

Advantageous Effects

According to the present invention, only one dose of the *Sarcodon aspratus* extracts of the present invention can cure dysmenorrhea, reduce a menstruation period, the amount of menstrual blood, menstrual irregularity, and the amount of extravasated blood, and clear the color of menstrual blood. Therefore, the *Sarcodon aspratus* extracts of the present invention can be used to prevent or treat gynecological diseases.

Best Mode

Hereinafter, the present invention will be described in detail.

The present invention provides a pharmaceutical composition for preventing or treating gynecological diseases, the pharmaceutic composition containing *Sarcodon aspratus* extracts as active ingredients.

The extracts may be prepared by a method including Step 1 of performing primary extraction by adding an extraction solvent to *Sarcodon aspratus*; Step 2 of performing secondary extraction of the primary extracts obtained in Step 1; Step 3 of filtering the extracts obtained in Step 2; and Step 4 of concentrating the filtered extracts of Step 3 under reduced pressure and drying the concentrated extracts.

According to the method, in Step 1, cultivated or commercial *Sarcodon aspratus* may be used without limitation, and the fruit body or mycelium of *Sarcodon aspratus* may be used. In one embodiment of the present invention, the *Sarcodon aspratus* extracts may be obtained from the fruit bodies of *Sarcodon aspratus*.

According to the method, in Step 1, the extraction solvent may be water, an alcohol, or a mixture thereof. Specifically, the alcohol may be a lower alcohol having $C_1$ to $C_4$. More specifically, the alcohol may be methanol or ethanol. In one embodiment of the present invention, the extraction solvent may be water. In addition, conventional extraction methods known in the art including low pressure and high temperature extraction, boiling water extraction, filtration, hot water extraction, immersion extraction, reflux extraction, cold extraction, steam extraction, room temperature extraction, and ultrasonic extraction may be used as an extraction method of the present invention. In one embodiment of the present invention, hot water extraction may be used as the extraction method of the present invention. The extraction solvent may be used in an amount of 30 to 90 times, preferably 40 to 80 times, more preferably 50 to 70 times, the dry weight of *Sarcodon aspratus*. In one embodiment of the present invention, the extraction solvent may be used in an amount of 60 times the dry weight of *Sarcodon aspratus*.

In Step 1, the primary extraction may be performed at 30° C. to 100° C., preferably 40° C. to 80° C., more preferably 45° C. to 60° C. In one embodiment of the present invention, the primary extraction may be performed at 50° C. In addition, the primary extraction may be performed for 5 minutes to 1 hour, preferably 15 minutes to 40 minutes, more preferably 25 minutes to 35 minutes. In one embodiment of the present invention, the primary extraction may be performed for 30 minutes.

In Step 2, the secondary extraction may be performed at 50° C. to 120° C., preferably 70° C. to 110° C., more preferably 90° C. to 105° C. In one embodiment of the present invention, the secondary extraction may be performed at 100° C. In addition, the secondary extraction may be performed for 5 minutes to 30 minutes, preferably 5 minutes to 20 minutes, more preferably 5 minutes to 15 minutes. In one embodiment of the present invention, the secondary extraction may be performed for 10 minutes.

The gynecological diseases may be diseases caused by an imbalance of female hormones. Specifically, the gynecological diseases may include dysmenorrhea, premenstrual syndrome, edema, menstrual irregularity, leukorrhea, extravasated blood, cold hands/feet syndrome, lower back pain, skin trouble, insomnia, alopecia, depression, dizziness, headache, constipation, diarrhea, hot flush, tinnitus, and urinary frequency, which are caused by an imbalance of female hormones.

In a specific embodiment of the present invention, the fruit bodies of *Sarcodon aspratus* were ground by hot air drying, and water was added to the ground fruit bodies to obtain *Sarcodon aspratus* extracts. The extracts were administered to 17 women in their teens to fifties who were taking painkillers due to severe dysmenorrhea during menstruation. As a result, for women taking the extracts, dysmenorrhea disappeared immediately after taking the *Sarcodon aspratus* extracts. In addition, in the month of taking the *Sarcodon aspratus* extracts once, a menstruation period and the amount of menstrual blood were reduced. In addition, the color of menstrual blood became clear, and extravasated blood disappeared (see Table 1). Furthermore, the following month after taking the *Sarcodon aspratus* extracts once, dysmenorrhea was mild or no dysmenorrhea occurred during menstruation even without taking the *Sarcodon aspratus* extracts, the amount of menstrual blood was reduced, and extravasated blood disappeared. The efficacy lasted even after 12 months (see Tables 2 to 4).

Therefore, the *Sarcodon aspratus* extracts may be used as a pharmaceutical composition for preventing or treating gynecological diseases.

The *Sarcodon aspratus* extracts according to the present invention as active ingredients may be contained in an amount of 10 to 95% by weight based on a total weight of the pharmaceutical composition. In addition to the active ingredients, the pharmaceutical composition of the present invention may further contain one or more active ingredients exhibiting the same or similar function as the active ingredients.

In addition, the composition of the present invention may include carriers, diluents, excipients, or combinations thereof conventionally used in preparation of biological agents. Pharmaceutically acceptable carriers are not particularly limited so long as the carriers are suitable for delivery of the composition. For example, the carriers may include compounds, saline solution, sterile water, Ringer's solution, buffered saline solution, dextrose solution, maltodextrin solution, glycerol, ethanol, or mixtures thereof described in the Merck Index, 13th ed. (Merck & Co., Inc.). In this case, other conventional additives such as antioxidants, buffers, and bacteriostatic agents may be added as necessary.

When formulating the composition, the composition is prepared using diluents or excipients such as fillers, extenders, binders, wetting agents, disintegrating agents, and surfactants that are generally used.

The composition of the present invention may be prepared as oral or parenteral formulations. Solid formulations for oral administration may include tablets, pills, powders, granules, capsules, troches, and the like. The solid formulations may be prepared by mixing one or more excipients such as starch, calcium carbonate, sucrose, lactose, and gelatin with one or more compositions. In addition, lubricants such as magnesium stearate and talc may be added. Meanwhile, liquid formulations may include suspensions, liquids for internal use, emulsions, or syrups. In this case, the liquid formulations may contain excipients such as wetting agents, sweeteners, fragrances, and preservatives.

Formulations for parenteral administration may include injections such as sterilized aqueous solutions, non-aqueous solvents, suspensions, and emulsions.

Vegetable oil such as propylene glycol, polyethylene glycol, and olive oil and injectable esters such as ethyl oleate may be used as the non-aqueous solvents or suspensions.

In addition, the present invention provides a functional health food for preventing or treating gynecological diseases, the functional health food containing Sarcodon aspratus extracts as active ingredients.

The extracts may be prepared by a method including Step 1 of performing primary extraction by adding an extraction solvent to Sarcodon aspratus; Step 2 of performing secondary extraction of the primary extracts obtained in Step 1; Step 3 of filtering the extracts obtained in Step 2; and Step 4 of concentrating the filtered extracts of Step 3 under reduced pressure and drying the concentrated extracts.

According to the method, in Step 1, cultivated or commercial Sarcodon aspratus may be used without limitation, and the fruit body or mycelium of Sarcodon aspratus may be used. In one embodiment of the present invention, the Sarcodon aspratus extracts may be obtained from the fruit bodies of Sarcodon aspratus.

The extracts may be extracted using water, an alcohol, or a mixture thereof as a solvent. Specifically, the alcohol may be a lower alcohol having $C_1$ to $C_4$. More preferably, the alcohol may be methanol or ethanol. In one embodiment of the present invention, the extraction solvent may be water.

The gynecological diseases may be diseases caused by an imbalance of female hormones. Specifically, the gynecological diseases may include dysmenorrhea, premenstrual syndrome, edema, menstrual irregularity, leukorrhea, extravasated blood, cold hands/feet syndrome, lower back pain, skin trouble, insomnia, alopecia, depression, dizziness, headache, constipation, diarrhea, hot flush, tinnitus, and urinary frequency, which are caused by an imbalance of female hormones.

In a specific embodiment of the present invention, the fruit bodies of Sarcodon aspratus were ground by hot air drying, and water was added to the ground fruit bodies to obtain Sarcodon aspratus extracts. The extracts were administered to 17 women in their teens to fifties who were taking painkillers due to severe dysmenorrhea during menstruation. As a result, for women taking the extracts, dysmenorrhea disappeared immediately after taking the Sarcodon aspratus extracts. In addition, in the month of taking the Sarcodon aspratus extracts once, a menstruation period and the amount of menstrual blood were reduced. In addition, the color of menstrual blood became clear, and extravasated blood disappeared (see Table 1). Furthermore, the following month after taking the Sarcodon aspratus extracts once, dysmenorrhea was mild or no dysmenorrhea occurred during menstruation even without taking the Sarcodon aspratus extracts, the amount of menstrual blood was reduced, and extravasated blood disappeared. The efficacy lasted even after 12 months (see Tables 2 to 4).

Therefore, the Sarcodon aspratus extracts may be used to prevent or treat gynecological diseases.

The content of the Sarcodon aspratus extracts as active ingredients added to the functional health food may be determined according to purpose. In general, the content may be 0.01 to 90 parts by weight based on a total weight of the functional health food.

In addition, there is no particular limitation on the form and type of the functional health food. For example, the functional health food may be prepared in the form of a tablet, a capsule, a powder, a granule, a liquid, or a pill.

The functional health food of the present invention may contain various flavors, natural carbohydrates, or the like as additional ingredients, as in the case of a general functional health food. The natural carbohydrates are monosaccharides such as glucose and fructose, disaccharides such as maltose and sucrose, polysaccharides such as dextrins and cyclodextrins, and sugar alcohols such as xylitol, sorbitol, and erythritol. The sweeteners may include natural sweeteners such as thaumatin and stevia extracts and synthetic sweeteners such as saccharin and aspartame.

In addition, the functional health food of the present invention may contain various nutritional supplements, vitamins, electrolytes, flavoring agents, coloring agents, pectic acid and salts thereof, alginic acid and salts thereof, organic acids, protective colloidal thickeners, pH regulators, stabilizers, preservatives, glycerin, alcohols, or the like. These components may be used independently or in combination. The content of the components may be 0.01 to 0.1 parts by weight based on 100 parts by weight of the extracts of the present invention.

In addition, the present invention provides a method of preventing or treating gynecological diseases including step of administering the Sarcodon aspratus extracts to a subject.

The Sarcodon aspratus extracts according to the present invention may have the characteristics as described above. The subject may be a mammal, specifically a human.

The composition of the present invention may be administered orally or parenterally according to a desired method. Parenteral administration may be selected from skin or intraperitoneal injection, rectal injection, subcutaneous injection, intravenous injection, intramuscular injection, and intrathoracic injection.

The composition according to the invention is administered in a pharmaceutically effective amount. The effective amount may vary depending on the type of disease, severity, drug activity, drug sensitivity, administration time, administration routes, release rate, treatment period, drugs used concurrently, and the like. The composition of the present invention may be administered alone or in combination with other therapeutic agents. In combination administration, administration may be performed sequentially or simultaneously.

To achieve the desired effect, the content of the active ingredients included in the pharmaceutical composition of the present invention may be 0.001 to 10,000 mg/kg, preferably 0.1 to 5 g/kg. The administration may be performed once or several times a day.

Furthermore, the present invention provides use of *Sarcodon aspratus* extracts for preparation of a pharmaceutical composition for preventing or treating gynecological diseases.

The *Sarcodon aspratus* extracts according to the present invention may have the characteristics as described above.

MODE FOR INVENTION

Hereinafter, the present invention will be described in detail through the following examples.

30 minutes, and then boiled at 100° C. for 10 minutes to obtain *Sarcodon aspratus* extracts.

<Experimental Example 1> Evaluation of Efficacy of *Sarcodon aspratus* Extracts in Treatment of Dysmenorrhea The following experiments were performed to evaluate the efficacy of *Sarcodon aspratus* extracts in alleviating or treating dysmenorrhea.

<1-1> Subject

The efficacy of the *Sarcodon aspratus* extracts in alleviating or treating dysmenorrhea was evaluated in 17 women in their teens to fifties who were taking painkillers due to severe dysmenorrhea during menstruation.

<1-2> Confirmation of Efficacy of *Sarcodon aspratus* Extracts in Treating Dysmenorrhea Based on Symptoms that Appear Before and After Taking *Sarcodon aspratus* Extracts To confirm change before and after administration of the *Sarcodon aspratus* extracts, women who usually took painkillers due to severe dysmenorrhea were selected, and at the onset of dysmenorrhea, the women took 160 ml of the extracts prepared according to Example 1. Changes according to extract intake are shown in Table 1 below.

TABLE 1

Comparison before and after taking *Sarcodon aspratus* extracts

| | Dysmenorrhea period | | Menstruation period | | Amount of menstrual blood | Color of menstrual blood | Extravasated blood | Menstrual irregularity | |
|---|---|---|---|---|---|---|---|---|---|
| No. | Before | Immediately after | Before | After | After | After | After | Before | After |
| 1 | 2 days | None | 5 days | 3 days | Decrease | Clear | Disappeared | Yes | No |
| 2 | 2 days | None | 7 days | 5 days | Decrease | Clear | Disappeared | No | No |
| 3 | 1 day | None | 7 days | 5 days | Decrease | Clear | Disappeared | No | No |
| 4 | 2 days | None | 5 days | 5 days | No change | Clear | Disappeared | No | No |
| 5 | 4 days | None | 7 days | 6 days | Decrease | Clear | Decreased | No | No |
| 6 | 3 days | None | 6 days | 4 days | Decrease | Clear | Disappeared | No | No |
| 7 | 3 days | None | 5 days | 5 days | Decrease | No change | Disappeared | No | No |
| 8 | 2 days | None | 6 days | 5 days | No change | Clear | Disappeared | No | No |
| 9 | 2 days | None | 5 days | 5 days | Decrease | Clear | Disappeared | No | No |
| 10 | 2 days | None | 5 days | 5 days | No change | Clear | Disappeared | No | No |
| 11 | 4 days | None | 6 days | 6 days | Decrease | Clear | Disappeared | No | No |
| 12 | 2 days | None | 5 days | 3 days | Decrease | Clear | Disappeared | Yes | No |
| 13 | 3 days | None | 5 days | 5 days | Decrease | Clear | Decreased | No | No |
| 14 | 1 day | None | 6 days | 4 days | Decrease | Clear | Disappeared | No | No |
| 15 | 2 days | None | 7 days | 5 days | No change | Clear | Decreased | No | No |
| 16 | 3 days | None | 7 days | 5 days | No change | No change | Disappeared | No | No |
| 17 | 2 days | None | 6 days | 4 days | Decrease | Clear | Disappeared | Yes | No |

However, the following examples are merely illustrative of the present invention, and the content of the present invention is not limited thereto.

EXAMPLE 1

Preparation of *Sarcodon aspratus* Extracts

*Sarcodon aspratus* was harvested from a hill located in Andong, Gyeongsangbuk-do. The fruit bodies of the harvested *Sarcodon aspratus* were subjected to hot air drying and pulverized. Then, 3 g of the pulverized *Sarcodon aspratus* was added to 180 ml of water, boiled at 50° C. for As shown in Table 1, immediately after taking the *Sarcodon aspratus* extracts, dysmenorrhea disappeared in all women who took the *Sarcodon aspratus* extracts. In most women, during the month of taking the *Sarcodon aspratus* extracts once, the menstruation period and the amount of menstrual blood decreased, the color of menstrual blood became clear, and extravasated blood and menstrual irregularity disappeared (Table 1). In addition, in some women, depression, fatigue, and edema due to menstruation decreased.

<1-3> Evaluation of Efficacy of *Sarcodon aspratus* Extracts in Treatment of Dysmenorrhea After Single Dose After taking *Sarcodon aspratus* extracts once, changes after 1, 2, 3, 6, and 12 months were examined, and the results are shown in Tables 2 to 4 below.

TABLE 2

Comparison of dysmenorrhea period

| No. | Dysmenorrhea period | | | | |
|---|---|---|---|---|---|
| | 1 month | 2 months | 3 months | 6 months | 12 months |
| 1 | None | None | None | None | None |
| 2 | 5 minutes | None | None | None | Unaware |
| 3 | None | None | None | None | None |
| 4 | None | None | None | None | None |
| 5 | Insignificant pain | None | None | Unaware | Unaware |
| 6 | None | None | None | None | None |
| 7 | None | None | None | None | None |
| 8 | None | None | None | None | None |
| 9 | None | None | None | None | None |
| 10 | None | None | None | None | None |
| 11 | None | None | None | None | None |
| 12 | None | None | None | Unaware | Unaware |
| 13 | None | None | None | None | None |
| 14 | None | None | None | None | None |
| 15 | None | None | None | None | None |
| 16 | None | None | None | None | None |
| 17 | None | None | None | None | None |

TABLE 3

Comparison of amount of menstrual blood

| No. | Amount of menstrual blood | | | | |
|---|---|---|---|---|---|
| | 1 month | 2 months | 3 months | 6 months | 12 months |
| 1 | Decrease | Decrease | Decrease | Decrease | Decrease |
| 2 | Decrease | Decrease | Decrease | Decrease | Unaware |
| 3 | Decrease | Decrease | Decrease | Decrease | Decrease |
| 4 | No change | No change | No change | No change | No change |
| 5 | Decrease | Decrease | Decrease | Unaware | Unaware |
| 6 | Decrease | Decrease | Decrease | Decrease | Decrease |
| 7 | Decrease | Decrease | Decrease | Decrease | Decrease |
| 8 | No change | Decrease | Decrease | Decrease | Decrease |
| 9 | Decrease | Decrease | Decrease | Decrease | Decrease |
| 10 | No change | No change | No change | No change | No change |
| 11 | Decrease | Decrease | Decrease | Decrease | Decrease |
| 12 | Decrease | Decrease | Decrease | Unaware | Unaware |
| 13 | Decrease | Decrease | Decrease | Decrease | Decrease |
| 14 | Decrease | Decrease | Decrease | Decrease | Decrease |
| 15 | No change | No change | No change | No change | No change |
| 16 | No change | No change | No change | No change | No change |
| 17 | Decrease | Decrease | Decrease | Decrease | Decrease |

TABLE 4

Comparison of generation of extravasated blood

| No. | Extravasated blood | | | | |
|---|---|---|---|---|---|
| | 1 month | 2 months | 3 months | 6 months | 12 months |
| 1 | Disappeared | Disappeared | Disappeared | Disappeared | Disappeared |
| 2 | Disappeared | Disappeared | Disappeared | Disappeared | Unaware |
| 3 | Disappeared | Disappeared | Disappeared | Disappeared | Disappeared |
| 4 | Disappeared | Disappeared | Disappeared | Disappeared | Disappeared |
| 5 | Decreased | Decreased | Disappeared | Unaware | Unaware |
| 6 | Disappeared | Disappeared | Disappeared | Disappeared | Disappeared |
| 7 | Disappeared | Disappeared | Disappeared | Disappeared | Disappeared |
| 8 | Disappeared | Disappeared | Disappeared | Disappeared | Disappeared |
| 9 | Disappeared | Disappeared | Disappeared | Disappeared | Disappeared |
| 10 | Disappeared | Disappeared | Disappeared | Disappeared | Disappeared |
| 11 | Disappeared | Disappeared | Disappeared | Disappeared | Disappeared |
| 12 | Disappeared | Disappeared | Disappeared | Unaware | Unaware |
| 13 | Decreased | Decreased | Disappeared | Disappeared | Disappeared |
| 14 | Disappeared | Disappeared | Disappeared | Disappeared | Disappeared |
| 15 | Decreased | Decreased | Decreased | Disappeared | Disappeared |
| 16 | Disappeared | Disappeared | Disappeared | Disappeared | Disappeared |
| 17 | Disappeared | Disappeared | Disappeared | Disappeared | Disappeared |

As shown in Tables 2 to 4, after taking the *Sarcodon aspratus* extracts once, dysmenorrhea was insignificant or absent even when no additional *Sarcodon aspratus* extracts were taken. In addition, the amount of menstrual blood was decreased, and extravasated blood disappeared. The efficacy lasted even after 12 months (Tables 2 to 4).

Meanwhile, the *Sarcodon aspratus* extracts according to the present invention may be formulated in various forms according to purpose. Several formulation methods of containing the *Sarcodon aspratus* extracts according to the present invention as active ingredients are described below, but the present invention is not limited thereto.

<Formulation Example 1> Preparation of Pharmaceutical Formulation

<1-1> Preparation of Powders 2 g of the *Sarcodon aspratus* extracts according to the present invention; and 1 g of lactose.

These components are mixed, a sealable bag is filled with the mixed components, and powders are prepared.

<1-2> Preparation of Tablets 100 mg of the *Sarcodon aspratus* extracts according to the present invention;

100 mg of corn starch;

100 mg of lactose; and 2 mg of magnesium stearate.

These components are mixed, and tablets are prepared by performing tableting according to a conventional method of preparing tablets.

<1-3> Preparation of Capsules 100 mg of the *Sarcodon aspratus* extracts according to the present invention;

100 mg of corn starch, 100 mg of lactose; and 2 mg of magnesium stearate.

These components are mixed, and capsules are prepared by filling capsules with gelatin according to a conventional method of preparing capsules.

<1-4> Preparation of Pills 1 g of the *Sarcodon aspratus* extracts according to the present invention;
1.5 g of lactose;
1 g glycerin; and
0.5 g of xylitol.

These components are mixed, and according to a conventional method, pills are prepared so that the weight of a pill is 4 g.

<1-5> Preparation of Granules 150 mg of the *Sarcodon aspratus* extracts according to the present invention;
50 mg of soybean extracts;
200 mg of glucose; and
600 mg of starch.

These components are mixed, 100 mg of 30% ethanol is added to the mixture, drying is performed at 60° C. to form granules, and bags are filled with the granules.

<1-6> Preparation of Injections 500 mg of the *Sarcodon aspratus* extracts according to the present invention;
an appropriate amount of sterile distilled water for injection; and
an appropriate amount of pH regulator;

These components are mixed, and according to a conventional method of preparing injections, injections are prepared so that one ampoule (2 ml) contains the components according to the contents.

<1-7> Preparation of Liquid Formulation 100 mg of the *Sarcodon aspratus* extracts according to the present invention;
10 g of isomerized sugar;
5 g of mannitol; and
an appropriate amount of purified water.

According to a conventional method of preparing liquid formulations, each component is dissolved in purified water, lemon flavor is added thereto, mixing is performed, purified water is added thereto to adjust the total volume to 100 ml, a brown bottle is filled with the mixture, and sterilization is performed to prepare a liquid formulation.

<Formulation Example 2> Preparation of Functional Health Food 100 mg of the *Sarcodon aspratus* extracts according to the present invention;
an appropriate amount of a vitamin mixture;
70 μg of vitamin A acetate;
1.0 mg of vitamin E;
0.13 mg of vitamin B1;
0.15 mg of vitamin B2;
0.5 mg of vitamin B6;
0.2 μg of vitamin B12;
10 mg of vitamin C;
10 μg of biotin;
1.7 mg of nicotinic acid amide;
50 μg of folate;
0.5 mg of calcium pantothenate;
an appropriate amount of a mineral mixture;
1.75 mg of ferrous sulfide;
0.82 mg of zinc oxide;
25.3 mg of magnesium carbonate;
15 mg of potassium phosphate monobasic;
55 mg of dicalcium phosphate;
90 mg of potassium citrate;
100 mg of calcium carbonate; and
24.8 mg of magnesium chloride.

The composition ratio of the vitamins and the mineral mixture described above may be determined according to a composition ratio used in general functional health foods, and the combination ratio of the vitamins and the mineral mixture may be arbitrarily determined. According to a conventional method of preparing functional health foods, these components are mixed, granules are prepared, and the granules are used to prepare a composition for a functional health food.

The invention claimed is:

1. A method of preventing or treating gynecological diseases, the method comprising:
   administering a pharmaceutical composition to a subject, wherein:
      the pharmaceutical composition comprises *Sarcodon aspratus* extracts as active ingredients;
      the gynecological diseases are diseases caused by an imbalance of female hormones;
      the gynecological diseases are one or more selected from the group consisting of dysmenorrhea, premenstrual syndrome, and menstrual irregularity;
      the *Sarcodon aspratus* extracts are prepared by a method including:
         a first step of performing primary extraction at 45° C. to 50° C. for five minutes to one hour by adding water as an extraction solvent to *Sarcodon aspratus*;
         a second step of performing secondary extraction at 90° C. to 105° C. for five minutes to twenty minutes of the primary extracts obtained in the first step;
         a third step of filtering the extracts obtained in the second step; and
         a fourth step of concentrating the filtered extracts of the third step under reduced pressure and drying the concentrated extracts; and
      the *Sarcodon aspratus* extracts are obtained from fruit bodies of *Sarcodon aspratus*.

2. A method of preventing or treating gynecological diseases, the method comprising:
   administering a functional health food to a subject, wherein:
      the functional health food comprises *Sarcodon aspratus* extracts as active ingredients;
      the gynecological diseases are diseases caused by an imbalance of female hormones;
      the gynecological diseases are one or more selected from the group consisting of dysmenorrhea, premenstrual syndrome and menstrual irregularity;
      the *Sarcodon aspratus* extracts are prepared by a method including:
         a first step of performing primary extraction at 45° C. to 50° C. for five minutes to one hour by adding water as an extraction solvent to *Sarcodon aspratus*;
         a second step of performing secondary extraction at 90° C. to 105° C. for five minutes to twenty minutes of the primary extracts obtained in the first step;

a third step of filtering the extracts obtained in the second step; and a fourth step of concentrating the filtered extracts of the third step under reduced pressure and drying the concentrated extracts; and the *Sarcodon aspratus* extracts are obtained from fruit bodies of *Sarcodon aspratus*.

\* \* \* \* \*